United States Patent
Van den Braak et al.

(10) Patent No.: US 9,492,502 B2
(45) Date of Patent: Nov. 15, 2016

(54) METHOD FOR PRODUCING A PROTEIN COMPRISING COMPOSITION WITH REDUCED DIGESTIVE COAGULATION

(71) Applicant: N.V. Nutricia, Zoetermeer (NL)

(72) Inventors: Claudia Catharina Maria Van den Braak, Utrecht (NL); Thomas Ludwig, Utrecht (NL); Marcel Minor, Wageningen (NL); Rudolph Eduardus Maria Verdurmen, Utrecht (NL); Hilde Ruis, Utrecht (NL)

(73) Assignee: N. V. Nutricia, Zoetermeer (NL)

( * ) Notice: Subject to any disclaimer, the term of this patent is extended or adjusted under 35 U.S.C. 154(b) by 0 days.

(21) Appl. No.: 14/413,685

(22) PCT Filed: Jul. 9, 2013

(86) PCT No.: PCT/NL2013/050519
§ 371 (c)(1),
(2) Date: Jan. 8, 2015

(87) PCT Pub. No.: WO2014/011039
PCT Pub. Date: Jan. 16, 2014

(65) Prior Publication Data
US 2015/0190464 A1    Jul. 9, 2015

(30) Foreign Application Priority Data

Jul. 9, 2012   (WO) ................ PCT/NL2012/050491

(51) Int. Cl.
| | | |
|---|---|---|
| *A23J 3/08* | (2006.01) | |
| *A23J 3/10* | (2006.01) | |
| *A23J 3/14* | (2006.01) | |
| *A23J 3/16* | (2006.01) | |
| *A61K 38/17* | (2006.01) | |
| *A23L 1/305* | (2006.01) | |
| *A23L 1/29* | (2006.01) | |
| *A61K 9/00* | (2006.01) | |
| *A61K 38/01* | (2006.01) | |
| *A61K 38/16* | (2006.01) | |

(52) U.S. Cl.
CPC ............. *A61K 38/1709* (2013.01); *A23J 3/10* (2013.01); *A23J 3/14* (2013.01); *A23J 3/16* (2013.01); *A23L 1/296* (2013.01); *A23L 1/305* (2013.01); *A23L 1/3053* (2013.01); *A23L 1/3055* (2013.01); *A23L 1/3056* (2013.01); *A61K 9/0095* (2013.01); *A61K 38/011* (2013.01); *A61K 38/018* (2013.01); *A61K 38/168* (2013.01); *A23V 2002/00* (2013.01)

(58) Field of Classification Search
None
See application file for complete search history.

(56) References Cited

U.S. PATENT DOCUMENTS

| | | | | | |
|---|---|---|---|---|---|
| 3,995,070 | A | * | 11/1976 | Nagasawa | A23J 3/10 426/456 |
| 4,053,642 | A | * | 10/1977 | Hup | C12N 1/20 426/36 |
| 4,883,682 | A | * | 11/1989 | Stein | A23J 3/10 426/424 |
| 2003/0104033 | A1 | * | 6/2003 | Lai | A23L 1/296 424/439 |
| 2009/0169712 | A1 | * | 7/2009 | Kanamori | A23B 7/005 426/656 |
| 2012/0189737 | A1 | * | 7/2012 | Andersen | A23C 3/03 426/41 |

FOREIGN PATENT DOCUMENTS

| | | | |
|---|---|---|---|
| EP | 1 314 361 A1 | 5/2003 | |
| EP | 1 762 147 A1 | 3/2007 | |
| EP | 1 972 346 A1 | 9/2008 | |
| NL | WO 2010126353 A1 * | 11/2010 | ............. A23L 1/296 |
| WO | WO-2006/029298 A1 | 3/2006 | |
| WO | WO-2007/063142 A1 | 6/2007 | |
| WO | WO-2009/046386 A1 | 4/2009 | |
| WO | WO-2010/131952 A1 | 11/2010 | |
| WO | WO 2013043873 A1 * | 3/2013 | ........... A23L 1/3055 |

OTHER PUBLICATIONS

International Search Report of PCT/NL2013/050519 mailed Nov. 14, 2013.
International Search Report of PCT/NL2013/050520 mailed Nov. 14, 2013.

\* cited by examiner

*Primary Examiner* — Jeffrey E Russel
(74) *Attorney, Agent, or Firm* — Foley & Lardner LLP; Sunit Talapatra

(57) ABSTRACT

A process of producing a composition comprising at least two different proteins is disclosed, of which at least one is a coagulating protein, such as a casein and/or a caseinate, and at least one is an anti-coagulating protein, such as a leguminous protein (for example pea and/or soy) combined or not with whey protein, comprising the steps of: a) heat-sterilizing a first liquid component comprising the coagulating protein, b) heat-sterilizing a second liquid component comprising the anti-coagulating protein, and c) mixing the first component with the second component to obtain a mixture thereof. The obtained mixture is useful as a food constituent having reduced coagulation in the upper gastro-intestinal tract, more in particular in the stomach.

17 Claims, 1 Drawing Sheet

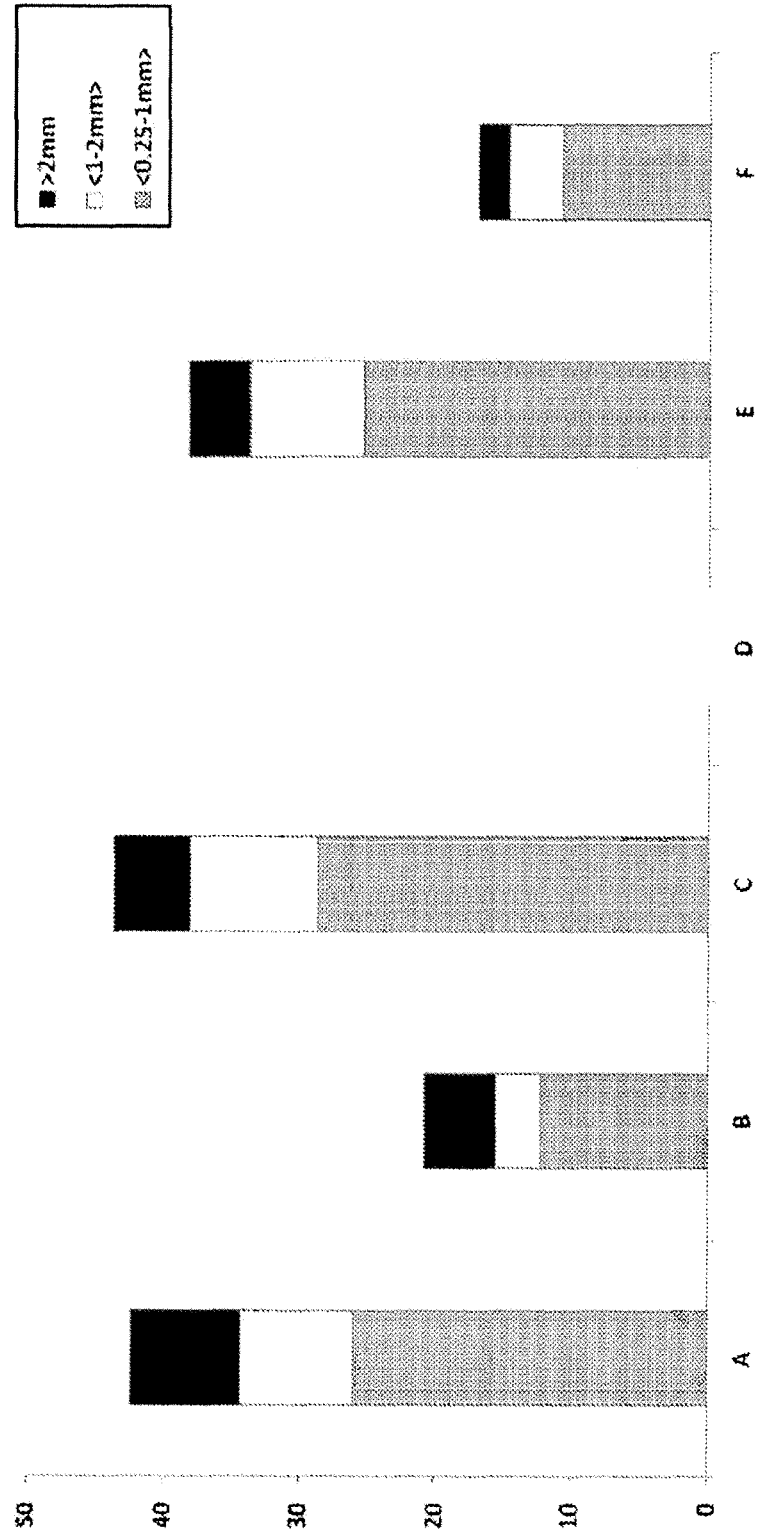

METHOD FOR PRODUCING A PROTEIN COMPRISING COMPOSITION WITH REDUCED DIGESTIVE COAGULATION

CROSS REFERENCE TO RELATED APPLICATIONS

The present application is a National Stage of International Application No. PCT/NL2013/050519, filed Jul. 9, 2013, which claims priority to International Application No. PCT/NL2012/050491, filed Jul. 9, 2012. The contents of these applications are herein incorporated by reference in their entirety.

FIELD OF THE INVENTION

This invention is in the field of protein-containing nutritional compositions. In particular, this invention concerns the coagulation of such compositions in the upper gastro-intestinal tract, more in particular in the stomach. This invention aims to modulate the digestive coagulation of proteins and peptic digestion, by adjusting the production process of nutritional compositions.

BACKGROUND OF THE INVENTION

Coagulation of proteins in the upper gastro-intestinal tract, in particular in the stomach, is hypothesised to delay gastric emptying. This can result in upper gastro-intestinal complications like reflux, gastrointestinal discomfort, aspiration pneumonia, but also to confer satiety and the feeling of having a full stomach when this is not intended yet. Nutritional compositions that mainly contain caseins are desired for their nutritional value, but these compositions in particular tend to coagulate under the acidic conditions encountered in the stomach.

One manner of providing digestion support to subjects in need thereof is to administer nutrition that results in lower coagulation levels in the stomach. The possibility to reduce digestive coagulation is preferred for those subjects suffering from upper gastrointestinal-related conditions such as intestinal discomfort, reflux, aspiration pneumonia, high gastric residual volume (GRV), vomiting, nausea, bloating, and delayed gastric emptying. Further, facilitating digestibility is desired when aiming to promote digestive comfort, reduce gastrointestinal cramping or colics. On the other hand, if slower release of stomach contents, slow absorption of nutrients, a certain level of fullness perception or satiety is intended, a certain level of coagulation of nutritional compositions within the stomach can be desirable. Therefore, having the ability to influence gastric coagulation levels can be desirable.

Nutritional compositions containing casein, in particular sodium caseinate and vegetable proteins such as soy and/or pea protein are known.

For example US 2003/0104033 teaches enteral formulations comprising 40-95 weight % of caseinate and 5-60 weight % of a stabilising protein, selected from the group of whey protein and one or more vegetable proteins selected from the group of soy, corn, potato, rice and pea, the most preferred vegetable protein being soy protein. The document is concerned with the reduction of creaming in enteral formulae and is silent with respect to coagulation properties of the composition.

Another example is EP 1 972 346 (WO2007/063142) which discloses a pea-based protein mixture comprising 50 weight % caseinate, 25 weight % whey proteins and 25 weight % pea protein. The document is silent with respect to coagulation properties of the composition.

Another example is WO2010/131952, wherein a method for reducing digestive coagulation of proteins is disclosed. Herein it is described that combining coagulating and anti-coagulating proteins in nutritional compositions reduces gastric coagulation effects.

SUMMARY OF THE INVENTION

The present inventors found that gastric coagulation of a given protein composition that contains a coagulating protein can be modulated by adjusting the production process of the nutritional composition. For instance, it was observed that reduction in coagulation was much more than was expected based on the ratio of coagulating and anti-coagulating proteins that were included in the composition. Thus by separately heat-sterilising a coagulating protein and an anti-coagulating protein, digestive coagulating of the protein fraction of a nutritional composition can be influenced to achieve desirably low coagulation levels.

The present invention therefore relates to a process of producing a composition, preferably a nutritional composition, comprising a mixture of at least two different proteins, of which at least one is a coagulating protein and one is an anti-coagulating protein, comprising the steps of:
  a) heat-sterilising a first liquid component comprising said coagulating protein,
  b) heat-sterilising a second liquid component comprising said anti-coagulating protein, and
  c) mixing said first component with said second component to obtain a mixture of said at least two different proteins.

Preferably, said mixture comprises an effective amount of anti-coagulating protein such that coagulation of said coagulating protein is reduced in the stomach of a subject. To this end, said mixture preferably has a weight ratio of said coagulating protein to said anti-coagulating protein of any value between 20:1 and 1:3. Preferably, this mixture is part of a nutritional composition.

Preferably, said first and/or said second liquid component further comprises a lipid, preferably selected from a vegetable oil, microbial oil (including algal oil) animal fat or fish oil.

Furthermore, the invention relates to a process of producing a composition comprising a mixture of coagulating and anti-coagulating proteins, preferably in a weight ratio of between 20:1 and 1:3, for reducing or preferably preventing coagulation in the upper gastrointestinal tract.

The process of the invention includes step a) which involves heat-sterilising said first liquid component which comprises said coagulating protein, preferably a casein, and includes step b) which involves heat-sterilising said second liquid component which comprises said anti-coagulating protein, preferably pea, soy whey—protein or a combination thereof, followed by mixing of the two components such that a composition is obtained which comprises a mixture of coagulating and anti-coagulating proteins in a weight ratio which is between 20:1 and 1:1.

Preferred coagulating proteins used in the process of the invention comprise (or preferably consist of) caseins. Preferred anti-coagulating proteins comprise (or preferably consist of) leguminous proteins (especially pea and/or soy) and—may additionally comprise—whey proteins. The process of the present invention can be performed such that a composition is obtained which comprises a mixture of coagulating proteins, preferably caseins, such as casein and/or a caseinate, and anti-coagulating protein, preferably pea or soy or whey protein or a combination thereof, having a weight ratio of coagulating to anti-coagulating proteins ranging between 20:1 and 1:1, preferably between 19:1 and 1:1, more preferably between 16:1 and 1:1, most preferably between 10:1 and 1:1.

Furthermore, the process of the invention may further comprise a drying step to obtain a dry composition, e.g. in the form of a powder. If a drying step is desired, it may be included after heat-sterilising the first and/or second liquid components of steps a) and b) but before the mixing thereof in step c), such that mixing is performed with at least the dried heat-sterilised first component and the dried heat-sterilised second component. Alternatively, such a drying step is performed after the heat-sterilised first liquid component is mixed with the heat-sterilised second liquid component in step c), such that mixing in step c) is performed with a liquid mixture of heat-sterilised coagulating and anti-coagulating proteins which is subsequently dried, for instance to obtain a powder.

Preferably, step c) as mentioned herein comprises the mixing of a heat-sterilised first liquid component with a heat-sterilised second liquid component to obtain a liquid mixture of coagulating and anti-coagulating proteins.

Another aspect of the invention relates to a composition obtainable by the process of the present invention. Said composition comprises at least two different proteins, of which at least one is a coagulating protein, preferably comprising or consisting of a casein, and of which at least one is an anti-coagulating protein, preferably comprising or consisting of pea or soy protein or a combination thereof or a combination thereof with whey protein. Said composition preferably comprises a mixture of coagulating to anti-coagulating proteins having a weight ratio which ranges between 20:1 and 1:1. The process of the invention is performed such that coagulating protein and anti-coagulating protein are separately heat-sterilised, i.e. without having been mixed with each other before the heat-sterilisation steps. Surprisingly, the composition obtainable by the process of the invention which comprises said mixture of coagulating and anti-coagulating proteins is characterised by having reduced coagulation properties when ingested.

Preferably, said mixture of anti-coagulating and coagulating proteins according to the present invention constitutes, in liquid form, between 1 and 20% (w/v), preferably between 2 and 15% (w/v), more preferably between 4 and 12% (w/v), most preferably between 5 and 10% (w/v) of the composition. Preferably said composition is a liquid nutritional composition suitable for enteral feeding.

Yet another aspect of the invention relates to the use of a composition obtainable by the process according to the invention for treating a person or patient experiencing gastric problems related to coagulation in the upper gastro-intestinal tract, in particular the stomach, by administering the composition obtainable by the process of the present invention to said person. The composition to be used for this purpose preferably contains an anti-coagulating protein selected from leguminous proteins and whey protein, especially from pea, soy and whey proteins.

Again another aspect of the present invention is concerned with a method of providing relief of gastric problems by administering or providing the composition obtainable by the process according to the present invention to a person. Consumption of the composition serves to lower coagulate particle size and/or reduce the number of coagulate particles in the stomach of said person or patient. This is expected to improve peptic digestion and gastric emptying of the stomach content of said person or patient. Thus, the invention further relates to the use of a composition obtainable by the process according to the present invention in the reduction or preferably prevention of coagulation in the upper gastro-intestinal tract, in particular the stomach, of the person or patient. The composition to be used preferably contains an anti-coagulating protein selected from leguminous proteins and whey protein, especially from pea, soy and whey proteins.

The invention also relates to the manufacturing of a composition according to the present invention, which composition has improved properties with respect to reduction or preferably prevention of coagulation in the stomach of a person or patient.

Yet another aspect of the present invention relates to a kit-of-parts, comprising a first holder containing a heat-treated coagulating protein obtainable by step a) and a second holder containing a heat-treated anti-coagulating protein obtainable by step b). Said first holder either comprises said coagulating protein in liquid form or in dry form. Conversely, said second holder comprises said anti-coagulating protein in either liquid or dry form.

DETAILED DESCRIPTION OF THE INVENTION

Process According to the Invention

This invention aims to reduce the digestive coagulation of proteins through the provision of an improved production process of providing protein-comprising nutritional compositions.

The present invention therefore relates to a process of producing a composition comprising a mixture of at least two different proteins, of which a first protein is a coagulating protein and of which a second protein is an anti-coagulating protein, comprising the steps of:
 a) heat-sterilising a first liquid component comprising said coagulating protein,
 b) heat-sterilising a second liquid component comprising said anti-coagulating protein, and
 c) mixing said first component with said second component to obtain a mixture of said at least two different proteins.

Preferably, said mixture has a weight ratio of said coagulating protein to said anti-coagulating protein of between 20:1 and 1:3.

Preferably, the first liquid component comprises said coagulating protein in an amount of at least 85 wt % of the total protein content of the first component.

Preferably, said mixture of coagulating and anti-coagulating proteins is part of a nutritional composition.

It is preferred that the mixing according to step c) of coagulating protein with anti-coagulating protein results in the provision of a mixture of coagulating protein (preferably a casein) and anti-coagulating protein (preferably pea or soy protein or a combination of 2 or 3 thereof) having a weight ratio of coagulating to anti-coagulating protein which is between 20:1 and 1:3.

It is to be understood that, within the context of the present invention, said heat-sterilisation steps a) and b) of the process of the invention are performed such that the first liquid component and the second liquid component are not mixed with each other during heating steps a) and b). To ensure that these components are kept separated as intended, said first and second liquid components are typically heat-sterilised in separate holders, containers or any other suitable means.

It is furthermore preferred that the second liquid component is substantially free of coagulating protein. Within the context of the present invention the phrase "substantially free of" is meant to be understood as that the second liquid component of step b) may comprise only a small amount of coagulating protein, such as preferably 4 wt % or less (or less than 3%, 2%, 1.5%, 1%, 0.5% or even less than 0.1%) relative to the total amount of protein present in the second liquid component.

Also, it is a preferred that the second liquid component comprises less than 30 wt. %, preferably less than 15 wt % more preferably less than 8 wt % or most preferably less than about 5 wt % of coagulating protein, in particular casein based on the total protein content of the second component, and most preferably is essentially free of coagulating protein such as casein.

The heat-sterilised liquid components used in steps a) and b) are preferably aqueous solutions, emulsions or dispersions containing said proteins in a concentration of between 0.1 and 20 wt % (w/v) (i.e. 1-200 g/l), preferably 1-20 wt %, more preferably 2-15 wt %, most preferably 4-12 wt % or even 5-10 wt %. Preferably, the pH thereof is in the range of 5-9, more preferably 6-8.

The amounts of anti-coagulating and coagulating proteins used in steps a) and b) are preferably selected such that the resulting mixture is characterised by a weight ratio of coagulating protein to anti-coagulating of between 20:1 and 1:3, preferably 19:1 and 1:2, more preferably 16:1 to 1:1, most preferably 10:1 to 1:1.

In one embodiment, the amount of coagulating protein in the first liquid component is between 0.5 and 19 wt %, preferably 1-14 wt %, more preferably 2-11 wt %, most preferably 3-9 wt %, whereas the amount of anti-coagulating protein in the second liquid component is between 0.05-10 wt %, preferably 0.1-8 wt %, more preferably 0.2-6 wt %, most preferably 0.3-5 wt %. Other values can be calculated on the basis of the preferred mixture of coagulating and anti-coagulating proteins and the amount thereof as used in the composition.

As a consequence of the separate heat-sterilising of said coagulating and anti-coagulating proteins in steps a) and b) of the process of the invention, mixing step c) is performed with heat-sterilised coagulating and anti-coagulating proteins which have not been in contact with each other prior to said mixing in the process of the invention. Said mixing in step c) preferably involves mixing of two liquid components comprising said mixture of coagulating and anti-coagulating proteins. Preferably, the pH of the resulting mixed liquid is in the range of 5-9, more preferably 6-8. In case a drying step is included in the process of the invention before said mixing in step c) takes place, said mixing in step c) preferably comprises mixing of dry first and second components to obtain a dry composition, such as a powder. In another embodiment the dry first component comprising the coagulating protein is mixed with said liquid second component comprising said anti-coagulating protein, or a liquid first component is mixed with a dry second component.

In the process of the present invention, heat-sterilisation of the first and second liquid components in step a) and b) is performed with any suitable method, such as retort sterilisation, ultra-high temperature (UHT) treatment or direct-steam injection (DSI). Heat-sterilisation comprises heating to a temperature of at least 80° C., preferably at least 100° C., most preferably at least 110° C. Preferably said temperature is applied for a sufficient period to accomplish sterilisation, e.g. at least 1 minute, in particular at least 5 minutes at 100° C., or shorter or longer depending on the temperature.

Heat-sterilisation of the first and/or second liquid components in step a) and/or b) of the process of the present invention can be preceded or followed by a homogenisation step. Homogenisation of said liquid components may be accomplished by the skilled person using methods known to him, such as shaking, stirring, inverting or vortexing of the liquid components at a suitable temperature for a suitable period of time such that a homogenised liquid is obtained. Thus, in a preferred embodiment of the invention, the heat-sterilisation of said first and/or second liquid components comprises heat-sterilisation of homogenised first and/or homogenised second liquid components, which are subsequently mixed in step c). In an alternative embodiment, the first and/or second liquid components are first heat-sterilised according to step a) and/or b), followed by a homogenising step of said liquid components, after which step c) is performed. In another alternative embodiment, the first and/or second liquid components are first heat-sterilised according to step a) and/or b), followed by mixing according to step c), after which the composition is subjected to a homogenising step of said liquid components.

In a further embodiment of the process of the invention, at least one drying step is included. Preferably, such a drying step takes place before the mixing in step c), such that the heated first liquid component and the heated second liquid component are dried, e.g. to obtain a powder, which components are subsequently mixed or dry blended. In this embodiment, step c) comprises mixing of dry or dried first and second component to obtain a dry mixture thereof. This powder is thus a mixture of separately heat-sterilised and dried coagulating and anti-coagulating proteins, which mixture has a dry weight ratio of said coagulating protein to said anti-coagulating protein of between 20:1 and 1:3.

Alternatively, the drying step of the process of the invention is included after the mixing in step c), wherein said liquid mixture of first and second liquid components is dried, e.g. to obtain a powder. This powder is thus a dried mixture of separately heat-sterilised coagulating and anti-coagulating proteins which mixture has a dry weight ratio of said coagulating protein to said anti-coagulating protein of between 20:1 and 1:3. As a further alternative a pre-drying step resulting in partially dried mixtures may precede mixing step c), and a post-drying step may follow resulting in a powder.

In a further embodiment of the process of the invention, the mixing in step c) is performed under sterile conditions. In a preferred embodiment, the process of the invention further comprises a step d), subsequent to step c), wherein the liquid product is aseptically filled into a holder. Such aseptically filling allows the liquid product to retain its shelf-life for a suitable time period.

In a preferred embodiment of the invention, further food components are added prior to, during or after performing any of the steps a), b) and/or c). Such further food components can be added to the heat-sterilised first and/or heat-sterilised second liquid components and subsequently mixed or added after the mixing of first and second components in step c), preferably followed by a homogenisation step. Preferably, said further food components are added in food-grade quality (meaning they are sterilised, pasteurised or filtrated) which obviates having to subject the composition to any further processing steps that could reduce the quality, shelf-life or stability et cetera of the composition.

Preferably, said first and/or said second liquid component further comprises a lipid, preferably selected from a vegetable oil, animal fat or fish oil. More preferably, said second liquid component of step b) comprises said lipid.

Such preferred lipids, include compounds containing fatty acids such as free fatty acids, their esters, monoglycerides, diglycerides, triglycerides, and phosphatides of mono- and diglycerides (phospholipids). Preferably at least 50 wt %, more preferably at least 80 wt. %, of the lipids comprises triglycerides. The fatty acids comprise saturated fatty acids, mono-unsaturated fatty acids and poly unsaturated fatty acids. The lipids may comprise fish oil, vegetable oil and/or animal fats, more preferably fish oil and/or vegetable oil such as palm oil, canola oil and sunflower oil. Preferred fish oils include long-chain omega-3 fatty acids, such as eicosapentaenoic acid (EPA), docosahexaenoic acid (DHA). Preferably, the lipids comprise between 5 and 35 wt. % of polyunsaturated fatty acids, comprising between 0.5 and 10 wt. % of alpha-linolenic acid (ALA).

In a preferred embodiment, said lipid comprises between 1 and 30 wt % (w/v) of the second liquid component of step b), more preferably between 3 and 20 wt %, most preferably between 4 and 15 wt %.

In the same or another embodiment, the first liquid component contains between 0 and 80 wt. %, preferably between 0 and 30 wt. %, more preferably between 0 and 10 wt. % of lipids on dry matter basis, in particular it is substantially free of lipids. In the same or a further embodiment, the second component contains between 10 and 90 wt. %, preferably between 20 and 80 wt. %, more preferably between 30 and 75 wt. % of lipids on dry matter basis. Preferably, the lipid to protein weight ratio in the first liquid component is between 0 and 4, preferably between 0 and 1, most preferably below 0.2. Preferably, the lipid to protein weight ratio in the second liquid component is between 0.4 and 5, preferably between 0.6 and 4, most preferably between 1 and 3.

The further food components typically comprise conventional food ingredients or constituents, such as digestible carbohydrates, fats, fibres, vitamins minerals, single amino acids, dipeptides, tripeptides and oligopeptides. In a preferred embodiment, the further food components are selected from at least 1 wt %, preferably at least 3 wt %, up to e.g. 18 wt % lipids, at least 1 wt %, preferably at least 4 wt %, up to e.g. 20 wt % of digestible carbohydrates and at least 0.1 wt %, preferably at least 0.5 wt. % of dietary fibres, up to e.g. 3 wt % based on the total weight of the first and/or second liquid component. Alternatively, the further food components are selected from at least 1 wt %, preferably at least 10 wt %, up to e.g. 200 wt % lipids, at least 1 wt %, preferably at least 10 wt %, up to e.g. 250 wt % of digestible carbohydrates and at least 0.1 wt %, preferably at least 1 wt. %, up to e.g. 25 wt % of dietary fibres, relative to the total weight of the mixture of proteins as obtained after step c).

In another embodiment of the invention, a further protein, such as defined herein below, is added to the process of the invention. Preferably, the amount of said further protein is lower than the level of coagulating protein. More preferably, the amount of said further protein is lower than both the level of coagulating protein and anti-coagulating protein. If present, said further protein, may be heat-sterilised together with the coagulating protein in step a), or together with the anti-coagulating protein in step b), or with both. Alternatively, the further protein, if present at all, may be separately heat-sterilised and added in step c) as a third component. Such a further protein serves a different purpose as influencing the coagulating status of the said mixture, for example, and if needed, to provide a source of amino acids which is complementary to the anti-coagulating and coagulating proteins, to improve organoleptic properties, or influence viscosity of the nutritional composition.

Product Obtainable by the Process of the Invention

The invention also pertains to a heat-sterilised mixture of coagulating and anti-coagulating proteins as a product obtainable by the process of the invention. In an embodiment, said mixture is comprised by a composition, in particular a nutritional composition. Preferably said mixture has a weight ratio of coagulating protein (preferably comprising or consisting of a casein, such as casein or caseinate or a combination thereof) to anti-coagulating protein (preferably comprising or consisting of pea or soy protein or a combination thereof) of between 20:1 and 1:1, or any ratio in between as mentioned herein. Preferably, said composition is in liquid form (as an aqueous solution, emulsion or dispersion), however, it can also be advantageous to have said composition in dry form, e.g. in the form of a powder. The composition comprising said mixture, in particular a nutritional composition, is preferably heat-treated, in particular sterilised or pasteurised, or (ultra) filtrated.

Furthermore, when said composition is in liquid form, the pH thereof preferably is in the range of 5-9, more preferably 6-8.

In a preferred embodiment, the heat-sterilisation of the liquid components in steps a) and b) is the final heat-treatment or sterilisation step before the composition is aseptically filled in at least one holder.

In a preferred embodiment, the mixture obtainable by the process of the invention is part of a composition which comprises further food components. Such further food components are preferably present in food-grade quality, meaning they are heat-treated (e.g. pasteurised or sterilised) and/or (ultra) filtrated. The further food components typically comprise conventional food ingredients or constituents, such as digestible carbohydrates, fibres, vitamins minerals, single amino acids, dipeptides, tripeptides and oligopeptides. In a preferred embodiment, the further food components are selected from at least 1 wt % digestible carbohydrates and at least 0.1 wt % dietary fibres, relative to the total weight of said mixture of coagulating and anti-coagulating proteins comprised by said composition.

Preferably, the product obtainable by the method of the invention further comprises a lipid, preferably selected from a vegetable oil, animal fat or fish oil.

Such preferred lipids include compounds comprising fatty acids as defined above. Thus, the lipid may comprise saturated fatty acids, mono unsaturated fatty acids (MUFA), poly unsaturated fatty acids (PUFA), long-chain polyunsaturated fatty acids (lcPUFA) such as EPA and DHA, and may be provided by fish oil, vegetable oil and/or animal fats, more preferably fish oil and/or vegetable oil such as palm oil, canola oil and sunflower oil.

In a preferred embodiment, said lipid comprises between 1 and 30 wt % (w/v), more preferably between 3 and 20 wt %, most preferably between 4 and 15 wt % of the liquid composition.

Preferably, the mixture of anti-coagulating and coagulating proteins constitutes, in liquid form, between 1 and 20% (w/v), preferably between 2 and 15% (w/v), more preferably between 4 and 12% (w/v), most preferably between 5 and 10% (w/v) of the composition, with or without further food components, preferably with further food components. More preferably, said composition is a nutritional composition, most preferably said composition is a liquid enteral nutritional composition.

Preferably, the coagulating protein is a casein which is present in an amount of at least 85 wt % of the total protein content of the first liquid component. Preferably, the coagulating protein is present in an amount of at least 50%, most preferably between 60 and 90 wt % of the total protein of the composition obtainable by the method of the invention.

In dry form, the contribution of the mixture of the anti-coagulating and coagulating proteins as a percentage of total weight of the composition depends on the presence of further food components as mentioned herein. The mixture of anti-coagulating and coagulating proteins can be used in a wide variety of food compositions, such as, but not limited to, enteral feeds, tube feeds, sip feeds or medical food, or used as an intermediate product for the manufacture of such feeds or food. Thus, where the dry form comprises further food components as mentioned herein, the amount of the mixture of anti-coagulating and coagulating protein constitutes between 1 and 99 wt % based on the total dry weight of the composition. Depending on the type of feed or food chosen, or its use as an intermediary product, the amount of the mixture of anti-coagulating and coagulating proteins varies between 5 and 95 wt %, 8 and 90 wt %, 10 and 70 wt %, 12 and 60 wt %, 13 and 50 wt %, 14 and 40 wt %, 15 and 30 wt % based on the total dry weight of the composition.

The relative amounts of proteins, digestible carbohydrates, fats and fibres comprised by the food composition obtainable by the invention as further components may vary according to the specific use and on whether it is a complete food or a food supplement. The protein portion thereof, in particular comprising said mixture according to the invention, in terms of energy (4 kcal/g) can e.g. be between 8 and 100 en. %. For a complete food said protein portion is preferably 8-40 en. %, more preferably 12-32 en. %, most preferably between 15 and 25 en. %.

In another embodiment of the invention, a further protein, such as defined herein below, is encompassed by the mixture of coagulating and anti-coagulating comprising nutritional composition. Preferably, the amount of said further protein in said composition is lower than the level of coagulating protein. More preferably, the amount of said further protein in said composition is lower than both the level of coagulating protein and anti-coagulating protein.

Kit-of-Parts

The invention furthermore relates to a kit-of-parts, said kit-of-parts comprising a first holder containing a heat-sterilised coagulating protein obtainable by step a) and a second holder containing a heat-sterilised anti-coagulating protein obtainable by step b). Preferably, the heat-sterilised first component and/or heat-sterilised second component is/are in a dry form, preferably as a powder. It will be clear that to obtain the composition in a dry form, the process of the invention comprises a drying step as mentioned herein. Alternatively, the heat-sterilised first component and/or heat-sterilised second component are in liquid form.

Preferably, the coagulating protein present in the first holder is a casein which is present in an amount of at least 85 wt % of the total protein content of the first holder.

Preferably, the first or second holder further comprises a lipid, preferably selected from a vegetable oil, animal fat or fish oil. Preferably, the lipid is comprised by the second holder.

Such preferred lipids include fatty acid comprising compounds, fatty acids, poly unsaturated fatty acids, unsaturated fatty acids, fish oil, vegetable oil and/or animal fats, more preferably fish oil and/or vegetable oil such as palm oil, canola oil and sunflower oil. Preferred fish oils include omega-3 fatty acids, such as eicosapentaenoic acid (EPA), docosahexaenoic acid (DHA) and alpha-linolenic acid (ALA).

In a preferred embodiment, said lipid comprises between 1 and 30 wt % (w/v), more preferably between 3 and 20 wt %, most preferably between 4 and 15 wt %.

The content of the first holder and the content of the second holder can be mixed such that a mixture is obtained which has a weight ratio of coagulating protein (preferably comprising or consisting of a casein, such as casein, caseinate and/or a combination thereof) to anti-coagulating protein (preferably comprising or consisting of pea, soy or optionally whey protein or a combination thereof) of between 20:1 and 1:3, preferably between 19:1 and 1:2, more preferably 16:1 to 1:1, most preferably 10:1 to 1:1. The contents of the first and second holder of said kit-of-parts are obtainable by performing steps a) and b) of the process according to the invention.

The first holder containing the heat-treated coagulating protein obtainable by step a) is preferably substantially free of anti-coagulating protein and the second holder containing heat-treated anti-coagulating protein obtainable by step b) is preferably substantially free of coagulating protein.

Preferably, the contents of the first holder, which includes any coagulating proteins, as well as the contents of the second holder, which includes any anti-coagulating proteins, are sterile.

Preferably, said first and/or said second holder comprises at least 1 wt % carbohydrates and/or 0.1 wt % dietary fibers. Vitamins and/or minerals can also be included in the first and/or second holder.

In case the content of the first and/or second holder(s) is in liquid form, the total protein content thereof is between 1 and 20% (w/v), preferably between 2 and 15% (w/v), more preferably between 4 and 12% (w/v), most preferably between 5 and 10% (w/v).

In case the contents of the first and/or second holder(s) is in dry form, the amount of the mixture of anti-coagulating and coagulating protein constitutes between 1 and 99 wt % based on the total dry weight of the composition, either as a total of the individual holders or as a total of the two holders together. More preferably, the amount of the mixture of anti-coagulating and coagulating proteins varies between 5 and 95 wt %, 8 and 90 wt %, 10 and 70 wt %, 12 and 60 wt %, 13 and 50 wt %, 14 and 40 wt %, 15 and 30 wt % based on the total dry weight of the composition.

In a preferred embodiment, the first and/or second holder of the kit-of-parts comprise(s) further food components. Such further food components are preferably present in food-grade quality, meaning they are heat-treated (e.g. pasteurised or sterilised) and/or (ultra) filtrated. The further food components typically comprise conventional food ingredients or constituents, such as digestible carbohydrates, fats, fibres, vitamins minerals, single amino acids, dipeptides, tripeptides and oligopeptides. In a preferred embodiment, the further food components are selected from at least 1 wt % fat, at least 1 wt % digestible carbohydrates and at least 1 wt % dietary fibres, relative to the total weight of said mixture of coagulating and anti-coagulating proteins comprised by said composition.

In another embodiment of the invention, a further protein such as defined below, is encompassed by first and/or second holder of the kit-of-parts. Preferably, the amount of said further protein in said first and/or second holder is lower than the level of coagulating protein. More preferably, the amount of said further protein in said first and/or second holder is lower than both the level of coagulating protein and anti-coagulating protein.

Coagulating Proteins

In general, coagulation means destabilisation or aggregation of proteins by decreasing their electric charge to that of the isoelectric point under the influence of acid and/or enzymes so that protein precipitates are formed. Coagulating proteins that are suitable or intended for nutritional compositions are known to the skilled person. In the context of the process and product obtainable by the present invention, the coagulating protein preferably is a casein, such as casein and/or caseinate. Herein a casein is to be construed as including casein, caseinate, micellar casein, sodium caseinate, calcium caseinate, potassium caseinate and magnesium caseinate. Preferably, said casein is an intact casein, e.g. intact casein and/or intact caseinate. Herein, intact coagulating protein in particular means non-hydrolysed coagulating protein, i.e. having a degree of hydrolysis of less than 2%.

Next to caseins as coagulating proteins, a protein is a coagulating protein if in the Gastric Digestion Test as described below, starting with a 6% (w/v) solution of said protein, a detectable amount thereof is present in particles with a diameter of more than 0.25 mm. Preferably, this amount is at least 10 wt % or even 30 wt % of said protein in particles with a diameter of more than 0.25 mm. More preferably, a protein is a coagulating protein if in the Gastric Digestion Test as described below, starting with a 6% (w/v) solution of said protein, a detectable amount thereof is present in particles with a diameter of more than 1 mm, preferably at least 10 wt % or even 30 wt % of such particles.

Gastric Digestion Test

To investigate the coagulation properties of protein-containing compositions, the Gastric Digestion Test according to Example 1 has been developed.

Briefly, a protein solution of 6 wt % (w/v) is incubated in the presence of artificial human saliva and artificial human gastric juice as defined herein under physiologically suitable conditions (i.e. at 37° C. under continuous stirring for 100 minutes), while controlling the pH such that the neutral starting pH of the protein solution (preferably a pH of 6) is reduced to a final pH of 2, after which the coagulate is size-fractioned and wet weight of the different fractions is determined. The wet weights of the different fractions represent a measure for the degree of coagulation.

The artificial human gastric juice as meant herein is a physiologically representative aqueous solution having 50 mM NaCl, 15 mM KCl, 1 mM $CaCl_2.H_2O$, 15 mM $NaHCO_3$, 0.014% (w/v) pepsin (e.g. porcine stomach, Sigma p7012), 0.019% (w/v) lipase (*Rhizopus oryzae*, DF 15K Amano Pharmaceutical Co, Ltd Nagoya), at a pH of 4.0, of which 45 ml is used in the Gastric Digestion Test. The artificial human saliva as meant herein is a physiologically representative aqueous solution having 100 mM NaCl, 30 mM KCl, 2 mM $CaCl_2.H_2O$, 0.065% (w/v) amylase (Sigma A 6211) having a pH of 6.3.

After incubation, the composition is divided in four fractions of different particle sizes using a sieve. These four fractions are characterised as a) having a particle size of 0.25 mm or less, b) a particle size of between 0.25 and 1 mm, c) a particle size of between 1 and 2 mm and d) a particle size of larger than 2 mm. Especially coagulates having a size larger than 1 mm, or larger than 2 mm, are believed to play a role in delay of gastric emptying. However, reducing the amount of total coagulate, meaning herein all particles with a size larger than 0.25 mm, is believed to facilitate peptic digestion. The amount of the individual wet weight fractions is determined by weighing each individual sieve with coagulate on it and subtracting the weight of the respective sieve.

Reduction of Coagulation by Anti-Coagulating Proteins

It has now been surprisingly found that the mixture of coagulating and anti-coagulating proteins obtained by the method of the present invention has reduced coagulation properties under the prevailing conditions of the upper gastrointestinal tract, in particular the acidic conditions of the stomach, compared to the same mixture which is obtained by first mixing and subsequently heat-sterilising both proteins.

It is to be understood that the reduction on coagulation of coagulating protein in the stomach means that the addition of an anti-coagulating protein or a mix thereof, to a coagulating protein or mix thereof, yields a synergistic effect on reduction of coagulation beyond what is expected arithmetically.

Anti-coagulation thus means herein that a protein has the effect of reducing the coagulation of the coagulating protein with which it is combined. This reduction effect on coagulation can be further characterised by the use of the herein described physiologically relevant Gastric Digestion Test. In a preferred embodiment, the anti-coagulating protein is characterised according to this digestion test, and qualifies as a protein which, when subjected to the method according to the present invention, reduces the size of coagulate particles in a synergistic manner. It preferably reduces the average size of coagulate particles of coagulating protein with a diameter of 0.25 mm or more in a detectable manner, compared to a processing method wherein the anti-coagulating protein is not absent during heat-sterilisation. Preferably, this reduction in the amount of particles with a size of 0.25 mm or more is at least 10 wt %. More preferably, the anti-coagulating protein reduces the amount of coagulate with particles of 1 mm or more in a detectable manner or by at least 10 wt %.

The reducing effect on coagulation is preferably determined using the Gastric Digestion Test with a 6% (w/v) solution of combined coagulating protein and sodium caseinate as anti-coagulating protein. Preferably, sodium caseinate is used in a weight ratio of 70:30 or 60:40 of sodium caseinate to anti-coagulating protein.

Anti-coagulating proteins are preferably selected such so as to provide an amino acid profile commensurate to the nutritional requirements of humans. In particular the anti-coagulating protein is selected to comply with the WHO amino acid profile recommendations for complete nutrition (see: WHO technical report series no. 935—Protein and amino acid requirements in human nutrition: report of a joint FAO/WHO/UNU expert consultation, 2007). Anti-coagulating proteins for example are selected from non-dairy proteins, preferably from vegetal and/or microbial proteins and combinations thereof. In the context of this invention "vegetal" relates to protein from plant origin, such as, for instance originating from vegetables such as carrot, pea, chickpea, green pea, cowpea, field pea, kidney bean, lupine, rice, soy, lentil, canola, hemp, zein, maize, corn, barley, flax, linseed, and wheat. Equivalent wording may be used such as "vegetable", or "plant-derived". In particular, the vegetal protein is derived from leguminous plants (Fabaceae family). Microbial proteins in particular comprise fungal or algal proteins.

According to a preferred embodiment, the anti-coagulating protein of the composition of the invention is a non-dairy protein. Preferably, the non-dairy protein is selected from the group consisting of vegetal proteins, fungal proteins and algal proteins. Preferred vegetal proteins include proteins obtained from cereals, legumes, brassicaceae, crucifers, solanaceae, fabaceae, carrot, hemp or linseed. Fungal proteins include proteins obtained from mushrooms or yeast.

More preferably, the anti-coagulating or vegetal protein is a legume (peas, beans) protein of the Fabaceae family, such as pea or soy protein, most preferably a pea protein as further defined below. The anti-coagulating proteins used in the composition of the invention are preferably intact, i.e. non-hydrolysed.

Whey protein is another suitable anti-coagulating protein according to the invention, which can be conveniently be part of the composition of the invention and its preparation in addition to a non-dairy protein, in particular to a legume protein, e.g. in a weight ratio of between 9:1 and 1:9, in particular between 4:1 and 1:4. Where the use of the composition of the invention for the treatment of gastric problems related to coagulation in the upper gastrointestinal tract is concerned, whey protein may be advantageously the anti-coagulating protein.

It is also envisaged that hydrolysed dairy or milk protein, in particular hydrolysed casein, can act as an anti-coagulating protein. Thus in one embodiment, the anti-coagulating protein is selected from hydrolysed dairy protein, hydrolysed milk protein, hydrolysed whey protein, hydrolysed casein, hydrolysed caseinate, or combinations thereof. Hydrolysed herein means the hydrolysed protein has been subjected to a hydrolysis step, in particular with a degree of hydrolysis of at least 2%, more in particular between 3 and 30%. Such hydrolysed proteins are readily available and commercialised as such on the market.

As defined herein, a further protein is a protein which is not considered a coagulating protein, based on the coagulating test described herein, and not considered an anti-coagulating protein, based on the anti-coagulation test described herein. Such a protein may be present in the compositions according to the invention as a further protein at a level which does not exceed 50% of the total weight of coagulating and anti-coagulating proteins, preferably less than 25% thereof. Such a further protein may be added in the process of the invention to the components in step a) and/or b), or mixed as a third component in step c). Preferably, such further proteins are added separate from the coagulating proteins, i.e. after step a) of the process of the invention, and more preferably also separate from the anti-coagulating proteins, i.e. after step b).

Specific Anti-Coagulating Proteins

For the purpose of the present invention, pea protein, preferably intact pea protein, is a preferred anti-coagulating protein. Preferably, pea protein is included in said mixture in an effective amount such that coagulation of said coagulating protein is reduced in the stomach of a subject.

Pea protein can be used effectively as anti-coagulating protein according to the process of the invention and product obtainable thereby in a wide range of coagulating to anti-coagulating protein weight ratios as indicated, such as 20:1 and 1:1 or between 16:1 and 1:1, or between 10:1 and 1:1, or between 4:1 and 1:1, or between 3:1 and 1:1, or between 10:1 and 1.5:1, or between 4:1 and 1.5:1, or between 3:1 and 1.5:1. Whey protein can also be used as an anti-coagulating protein in said process and product obtainable thereby, in particular in addition to one or more non-dairy proteins, especially leguminous proteins. If present, whey protein is preferably included in said mixture in an effective amount such that coagulation of said coagulating protein is further reduced in the stomach of a subject. More preferably, whey protein is included in relatively small amounts (e.g. between 10:1 and 1:1, or between 4:1 and 1:1, or between 3:1 and 1:1, or between 10:1 and 1.5:1, or between 4:1 and 1.5:1, or between 3:1 and 1.5:1) which already suffice to obtain a pronounced reduction in gastric coagulation. Thus, in a preferred embodiment, the anti-coagulating protein consists of pea and optionally additionally whey protein.

Pea protein is relatively inexpensive (on average, pea protein may cost about half the price of caseinates) and as it is added to the nutritional composition it increases the protein content while keeping costs quite low. Pea protein is generally tolerated well by most people, it is lactose-free and is not a common allergen. Pea protein is quite high in cysteine content and can therefore compensate the inadequate amount of cysteine in caseins. Furthermore, pea protein is quite high in arginine compared to casein, which is required for muscle metabolism and which facilitates the intake of body mass while reducing body fat; and it is quite high in lysine, when compared to the other vegetable proteins specially when derived from cereals/grains, which is needed to build protein muscle and assist in the maintenance of lean body mass.

Several pea sources are readily available to the skilled person, for example, from Roquette (Lestrem, France) which markets a pea isolate obtained from the yellow pea (*Pisum sativum*), and from Cosucra Groupe Warcoing (Warcoing, Belgium). Other pea protein sources may originate from green pea (*Pisum sativum*), cowpea (*Vigna unguiculata*), chickpea (*Cicer arietinum*), and field pea (*Pisum arvense*).

In one embodiment according to the invention, the pea protein is substantially in intact form or non-hydrolysed. In another embodiment according to the invention, the pea protein is fermented pea protein or is pea protein hydrolysate.

In the context of this invention, a "non-hydrolysed" protein is equivalent to an "intact" protein, meaning that the protein has not been subjected to a hydrolysis process. However, minor amounts of hydrolysed proteins may be present in the source of non-hydrolysed proteins. In this context, "minor" should be understood as an amount of 10 weight % or less. The term "about" should be interpreted as a deviation of plus or minus 10% of the given value.

For the purpose of the present invention, soy protein, preferably intact soy protein, is another preferred anti-coagulating protein. Preferably, soy protein is included in said mixture in an effective amount such that coagulation of said coagulating protein is reduced in the stomach of a subject. Soy protein can be used in the process of the invention and included in the product obtainable thereby in a wide range of the ratios as indicated herein, ranging between 20:1 and 1:1. The preferred ratio of coagulating protein to soy protein is such that moderate levels (e.g. between 10:1 and 1:1, or between 4:1 and 1:1, or between 3:1 and 1:1, or between 10:1 and 1.5:1, or between 4:1 and 1.5:1, or between 3:1 and 1.5:1) of soy protein provide the most pronounced anti-coagulating effect. In a preferred embodiment, the anti-coagulating protein consists of soy protein, or consists of a combination with pea and/or whey protein.

Soy protein is a vegetable protein that contains the essential amino acids in a relatively high proportion for human health. Several soy sources are readily available to the skilled person, for example, from The Solae Company (St. Louis, Mo., USA).

In one embodiment according to the process or product of the invention, the soy protein is substantially in intact form or non-hydrolysed.

In another embodiment according to the process or product of the invention, the soy protein is fermented soy protein, or soy protein hydrolysate.

Mixture of Coagulating and Anti-Coagulating Protein

The mixture of anti-coagulating and coagulating proteins according to the present invention in all its aspects (i.e. obtained by the process of the invention, encompassed by the composition obtainable by the process of the invention, and comprised by the kit-of-parts of the invention), has a preferable weight ratio of coagulating protein to anti-coagulating protein of between 20:1 and 1:3. Preferably, this weight ratio is between 19:1 and 1:2, 18:1 and 1:1.5, 17:1 and 1:1.25, 16:1 and 1:1, 15:1 and 1:1, 14:1 and 1:1, 13:1 and 1:1, 12:1 and 1:1, 11:1 and 1:1, 10:1 and 1:1, 9:1 and 1:1, 8:1 and 1:1, 7:1 and 1:1, 6:1 and 1:1, 5:1 and 1:1, 4:1 and 1:1, 3:1 and 1:1, 2:1 and 1:1.

Alternatively, the upper limit of this range of said coagulating protein, in particular a casein (e.g. casein or caseinate), to said anti-coagulating protein (e.g. pea, soy or whey—protein or a combination thereof), expressed as weight ratio, in said mixture is 20:1, 19:1, 18:1, 17:1, 16:1, 15:1, 14:1, 13:1, 12:1, 10:1, 9:1, 8:1, 7:1, 6:1, 5:1, 4:1, 3:1, or 2:1. Conversely, the lower limit of this range of said coagulating protein (e.g. casein or caseinate) to said anti-coagulating protein (e.g. pea, soy or whey protein or a combination thereof), expressed as a weight ratio, in said mixture is 1:1, or 1.2:1, or 1.5:1, or, 1.8:1, or 2:1, or 2.2:1, or 2.5:1, or 2.8:1 or 3:1. Preferably, the weight ratio of said coagulating protein (e.g. casein or caseinate) to said anti-coagulating protein (e.g. leguminous or whey protein, in particular pea or soy protein or a combination thereof or a combination thereof with whey protein) in said mixture is about 20:1, or about 19:1, or about 18:1, or about 17:1, or about 16:1, or about 15:1, or about 14:1, or about 13:1, or about 12:1, or about 10:1, or about 9:1, or about 8:1, or about 7:1, or about 6:1, or about 5:1, or about 4:1, or about 3:1 or about 2:1 or about 1:1, or about 1:1.5, or about 1:2. It is within the capabilities of the skilled person to establish what exact ratio is preferred to reduce the gastric coagulation properties of a given coagulating protein by selecting an amount and type of anti-coagulating protein using the Gastric Digestion Test as meant herein.

Alternatively, the ratio of coagulating protein, in particular a casein (e.g. casein or caseinate), to anti-coagulating protein (e.g. leguminous or whey protein, in particular pea or soy protein or a combination thereof) of said mixture is between 95:5 and 25:75, expressed as wt % coagulating protein to wt % anti-coagulating protein in the mixture obtained in step c). More preferably, this ratio is between 90:10 and 33:67, 85:15 and 40:60, 70:30 and 50:50 or between 60:40 and 50:50.

Preferably, the composition obtainable by the process of the invention is a liquid composition which comprises said mixture of coagulating and anti-coagulating protein obtainable by step c).

The amount of the protein mixture obtainable by step c) as included in the liquid composition comprises between 1 and 20% (w/v) of said liquid composition, preferably between 2 and 15% (w/v), more preferably between 4 and 12% (w/v), most preferably between 5 and 10% (w/v) of said liquid composition. More specifically, the amount of the protein mixture as obtainable by step c) of the invention comprises 1, 2, 3, 4, 5, 6, 7, 8, 9, 10, 11, 12, 13, 14, 15, 16, 17, 18, 19 or 20% (w/v) of said liquid composition. Most preferably, the protein content of the liquid composition 6% (w/v).

In case the composition obtainable by the process of the invention is a dry composition, e.g. a powder, the amount of the mixture obtainable by step c) as included in the dry composition comprises at least 4 wt. % based on the total dry weight of the composition. More preferably this amount is at least 5 wt. %, at least 6 wt. %, at least 8 wt. %, at least 10 wt. %, at least 15 wt. %, at least 20 wt. %, at least 25 wt. %, at least 30 wt. % or at least 40 wt. % based on the total dry weight of the composition. Preferably, this amount is not more than 95 wt. % based on the total dry weight of the composition, preferably not more than 90 wt. %, preferably not more than 85 wt. %, preferably not more than 80 wt. %, preferably not more than 75 wt. %, preferably not more than 70 wt. %, preferably not more than 65 wt. %, and preferably not more than 60 wt. % based on the total dry weight of the composition.

Applications

Due to a variety of reasons, such as diseases, medical conditions, malnutrition, medical disabilities, post-surgery etc., patients may not be able to obtain the necessary nutrition by ingesting food orally, by eating or drinking. Therefore, it has been known to provide medical enteral nutrition by oral nutritional supplements or tube feeding. Tube feeding is given to provide nutrition to patients which cannot obtain nutrition by swallowing, using a device such as a nasogastric feeding tube or a naso jejunal feeding tube, or by using a percutaneous endoscopic gastrostomy (PEG) or PEG-jejuno-feeding system. In the context of this application, the state of being fed by nutritional supplements and/or a by a feeding tube is called enteral feeding, comprising all of the abovementioned tube feeding systems, and the nutrition used in the feeding by nutritional supplements and/or a by a feeding tube is called enteral nutrition. Use of such enteral nutrition may be temporary for the treatment of acute conditions, or lifelong in the case of chronic disabilities. In the latter case, it is primordial that the enteral nutrition is designed for long-term administration containing all necessary components.

In one embodiment, the composition comprising the mixture of anti-coagulating and coagulating protein obtainable by the method of the present invention is used for reduction, prevention or treatment of upper gastrointestinal complications such as, e.g. gastrointestinal reflux, intestinal discomfort, reflux, aspiration pneumonia, high gastric residual volume, vomiting, nausea, bloating, digestive discomfort, gastrointestinal cramping, colics, coagulation in the upper gastrointestinal tract and/or delayed gastric emptying, especially in vulnerable people, such as hospitalised patients.

In a preferred embodiment, said composition comprising said mixture of the invention is a nutritional composition which is administered to humans, preferably to humans that benefit from receiving easily digestible nutrition, preferably to humans with digestive tract complications, preferably to humans with digestive problems, preferably to hospitalised patients, preferably to a person that is in a disease state, a person that is recovering from a disease state, a person that is malnourished, a baby, an infant and/or a toddler. Preferably, said administering involves oral administration, by eating or drinking, preferably enterally by tube feeding, of the composition with the mixture of the present invention.

In one aspect, the invention concerns the use of anti-coagulating protein in the manufacture of a nutritional composition that further comprises coagulating protein, for the reduction, prevention or treatment of upper gastrointestinal conditions or complications selected from the group of reflux, aspiration pneumonia, high gastric residual volume (GRV), vomiting, nausea, bloating, and delayed gastric emptying.

In one aspect, the invention concerns the use of anti-coagulating proteins, preferably one or more leguminous proteins, or whey protein or a combination thereof, in the manufacture of a nutritional composition that further comprises coagulating protein, preferably a casein, such as caseinate or casein, for use in preventing or reducing of coagulation in the stomach of said coagulating protein.

In one aspect, the invention concerns the use of anti-coagulating proteins, preferably pea protein, soy protein, whey protein or a combination thereof, in the manufacture of a nutritional composition that further comprises coagulating protein, preferably a casein, such as caseinate or casein, for the reduction, prevention or treatment of upper gastrointestinal complications such as, e.g. gastrointestinal reflux, intestinal discomfort, reflux, aspiration pneumonia, high gastric residual volume, vomiting, nausea, bloating, digestive discomfort, gastrointestinal cramping, colics, coagulation in the upper gastrointestinal tract and/or delayed gastric emptying, especially in vulnerable people, such as hospitalised patients.

Another category of subjects that can benefit from the present method are infants. Thus in one embodiment according to the present invention the nutritional composition is an infant formula, a follow-on formula and/or a toddler formula. In one embodiment according to the present invention the nutritional composition is in a suitable form for administration to a baby, an infant and/or a toddler.

In one embodiment according to the present invention the nutritional composition is to promote digestive comfort, reduce gastrointestinal cramping and/or reduce colics.

Preferably, the mixture of the invention comprised by a (nutritional) composition can be used to partially or fully replace, or supplement, the typical daily intake by a person of coagulating proteins (i.e. caseins and/or caseinates) which are produced by conventional methods, i.e. methods not including the combination of separately heat-sterilising coagulating and anti-coagulating proteins in steps a) and b), with the mixing thereof in step c) according to the present invention. Preferably, the amount of the mixture of the invention included in the diet of a person experiencing gastric problems related to coagulation in the upper gastrointestinal tract, in particular the stomach, is such that coagulation-related problems experienced by that person are reduced or preferably prevented.

The composition according to the invention comprising said mixture preferably has the form of a complete food, i.e. it can meet all nutritional needs of the user. As such, the composition is preferably in the form of a liquid, more preferably a liquid enteral composition according to the invention, and as such preferably contains 1000 to 2500 kcal per daily dosage. Depending on the condition of the patient, a daily dose is about 25 to 35 kcal/kg bodyweight/day. Therefore, a typical daily dose for a 70 kg person contains about 2000 kcal. The complete food can be in the form of multiple dosage units, e.g. from 8 (250 ml/unit) to 2 units (1 l/unit) per day for an energy supply of 2000 kcal/day using a liquid enteral composition according to the invention of 1.0 kcal/ml. Preferably, the composition is adapted for tube feeding.

Although a complete food composition of the invention may, in addition to the protein mixture of the invention comprising at least one coagulating protein and at least one anti-coagulating protein, contain further proteins sources, it is preferred that the proteins mixture of the invention is the only protein source. The protein mixture of the invention preferably contributes to between 5 and 40 en. %, more preferably between 8 and 32 en. %, most preferably between 15 and 25 en. % of the complete food. The daily dosage of the protein mixture of the invention is preferably between 3 kcal and 10 kcal per kg bodyweight, more preferably between 4 and 8 kcal per kg bodyweight, or preferably between 0.75 and 2.5 g protein mixture, preferably between 1 and 2 g per patient per day, as part of a complete food.

Preferably, the composition is packaged, stored and provided in a container such as plastic bag or a pouch or the like. A variety of such containers is known, for example 500 ml, 1000 ml, and 1500 ml containers are known in the art. It should be noted that any suitable container can be used to package, store and provide the nutritional composition according to the invention.

In one embodiment of the present invention, the composition is provided in a ready to use liquid form and does not require reconstitution or mixing prior to use. The composition according to the invention can be tube fed or administered orally. For example, the composition according to the invention can be provided in a can, on spike, and hang bag. However, a composition may be provided to a person in need thereof in powder form, suitable for reconstitution using an aqueous solution or water such that the composition according to the invention is produced. Thus in one embodiment of the present invention, the present composition is in the form of a powder, accompanied with instructions to dissolve or reconstitute in an aqueous composition or water to arrive at the liquid enteral composition according to the present invention. In one embodiment of the present invention, the present liquid enteral composition may thus be obtained by dissolving or reconstituting a powder, preferably in an aqueous composition, in particular water.

The invention will now be further elucidated by several examples, without being limited thereto or thereby.

FIGURES

FIG. 1 shows the absolute wet weight of coagulates between 0.25 mm and 1 mm (lower part, grey bars), between 1 mm and 2 mm (middle part, open bars) and larger than 2 mm (upper part, black bars), after 100 minutes of gastric digestion of different protein mixtures of sodium caseinate with whey or pea protein. A: Na-cas:whey=90:10; heat-sterilised as protein mixture (pre-mixed), B: same ratio, separately heat-sterilised proteins (post-mixed). C: Na-cas:pea=70:30; heat-sterilised as protein mixture, D: same ratio, separately heat-sterilised proteins. E: Na-cas:pea=60:40; heat-sterilised as protein mixtures, F: same ratio, separately heat-sterilised proteins. A measurable reduction in coagulation was demonstrated to occur with pre-heating (post-mixing) for all parameters shown.

EXAMPLES

Example 1

Preparation of Caseinate, Pea, Soy and Whey Protein Mixtures

Commercially available canola oil, sodium caseinate with a protein content of 88 wt %, and pea protein with a protein content of 78 wt % were used as starting materials for obtaining the solutions as prepared.

Protein solutions with a protein concentration of 6 wt % (w/v) and different weight ratios of sodium caseinate and pea protein (70:30, 60:40) were prepared by dissolving the required amount of protein in demineralised water. Either a single sodium caseinate and pea protein solution was prepared before sterilisation, or two separate solutions were prepared that were mixed after heat-sterilisation.

After the initial dissolving of the proteins, the pH was adjusted to 8.0 using potassium hydroxide. Subsequently the solutions were heated for 30 seconds at 85° C., which was followed by a homogenisation step. After the pasteurisation step pH was again adjusted to pH 8.0 and the dry matter content was adjusted to come to a final protein content of all solutions of 6 wt % (w/v). Finally the products were filled in 200 ml glass bottles which were retort sterilised for 16 minutes at 121.5° C.

Premixed heat-sterilised protein solutions were used without further processing steps in the Gastric Digestion Test. Alternatively, heat-sterilised protein solutions comprising only sodium caseinate or pea protein were combined after heat-sterilisation. Before the start of the coagulation experiments, the heat-sterilised caseinate solution and the heat-sterilised pea protein solution were combined in the required ratio and carefully mixed by shaking.

The same procedure used for pea protein was followed using soy protein with a protein content of 88 wt %, instead of pea protein. When using whey protein, a starting material with a protein content of 83 wt % was used.

Gastric Digestion Test

Stomach digestion and coagulation was mimicked over 100 minutes in a computer controlled substrate pump setup (Multifermentor fed-batch; DASGIP AG, Juelich, Germany) at 37° C. upon continuous stirring.

For each experiment, 150 ml of protein solution was used as the starting volume. Per experiment, a total of 45 ml of artificial gastric juice (50 mM NaCl, 15 mM KCl, 1 mM $CaCl_2.H_2O$, 15 mM $NaHCO_3$, 0.014% (w/v) pepsin (porcine stomach, sigma p7012), 0.019% (w/v) lipase (*Rhizopus oryzae*, DF 15K Amano Pharmaceutical Co, Ltd Nagoya); pH 4.0) was added. The gastric juice was added in two steps with different flow rates. In the first two minutes, a flow rate of 225 ml/h was used. For the rest of the experiment the flow rate was 23 ml/h. In addition, in the first 60 minutes of the experiment a total of 30 ml of artificial saliva (100 mM NaCl, 30 mM KCl, 2 mM $CaCl_2.2H_2O$, 15 mM $NaHCO_3$, 0.065% (w/v) α-amylase (Sigma A 6211); pH 6.3) was added continuously to the solution at a constant rate.

The pH was decreased over 100 minutes from a pH of 6.6 at start to a final pH of 2.0 (pH at start=6.6, pH at 8 minutes=5.0, at 15 minutes=4.0, at 42 minutes=3.0, at 100 minutes=2.0) by the addition of 1 M HCl upon continuous mixing. If necessary, acidification was automatically corrected by the addition of an alkaline solution (1 M $NaHCO_3$, 3 M NaOH).

Determination of Coagulate

After gastric digestion, each sample was poured over metal sieves to yield fractions with particle sizes of a) larger than 2 mm, b) below 2 mm and above 1 mm, c) below 1 mm and above 0.25 mm and d) below the limit of 0.25 mm. In short, the wet weight fractions were determined by weighing each individual respective sieve with coagulate on it and subtracting the weight of each sieve.

Control Results

High coagulate wet weight levels are observed after 100 minutes of stomach digestion using sodium-caseinate at a concentration of 6 wt % (w/v) as the sole protein (data not shown).

Sample Results

After subjecting samples to the treatment as mentioned under "Preparation of caseinate, pea, soy and whey mixtures", the following results were obtained after the Gastric Digestion Test.

Whey protein, which was heat-sterilised as a mixture with sodium caseinate in a 90:10 weight ratio gave a total amount of coagulate which was similar to samples wherein only sodium caseinate was used (A, FIG. 1, data wherein sodium caseinate was used is not shown). However, when the same mixture of whey protein to sodium caseinate of 90:10 was obtained by first heat-sterilising followed by mixing said proteins, coagulate amounts of each individualised fraction and total coagulate wet weight were significantly reduced (B, FIG. 1). Similar considerations hold for pea (FIG. 1: C vs D and E vs F) as anti-coagulating proteins, not only at 90:10 ratio, but over a broader range of ratios as well (70:30 and 60:40). Also, a reduction of total coagulate form about 36 to about 33 was found using casein:soy 60:40.

Test for Anti-Coagulating Proteins

A protein under investigation is considered to be anti-coagulating according to the present invention, if in the experiment above (the Gastric Digestion Test of Example 1) a mixture of the heat-sterilised protein and a separately heat-sterilised coagulating protein (in particular casein) produces an amount of wet weight coagulate fraction larger than 0.25 mm which is at least 10% less than the amount produced by the same protein mixture prepared by first mixing the two different protein components followed by heat-sterilising the mixed protein components.

It should be understood that various changes and modifications to the presently preferred embodiments described herein will be apparent to those skilled in the art. Such changes and modifications may be made without departing from the spirit and scope of the invention and without diminishing its advantages. It is therefore intended that such changes and modifications are covered by the appended claims.

The invention claimed is:

1. A process of producing a composition comprising a mixture of at least two different proteins, of which at least one is a coagulating protein and at least one is an anti-coagulating protein, the process comprising:
   (a) heat-sterilising a first liquid component comprising the coagulating protein,
   (b) heat-sterilising a second liquid component comprising the anti-coagulating protein, and
   (c) mixing the first component with the second component to obtain a mixture of the proteins,
   wherein (a) and (b) are performed separately,
   wherein the mixture has a weight ratio of the coagulating protein to the anti-coagulating protein between 20:1 and 1:1, and wherein the mixture of coagulating and anti-coagulating protein, in the Gastric Digestion Test of Example 1, produces an amount of wet weight coagulate fraction larger than 0.25 mm which is at least 10% less than the amount produced by the same protein mixture prepared by first mixing the two different proteins followed by heat-sterilising the mixed proteins.

2. The process according to claim 1, wherein the first and/or the second liquid component further comprises a lipid.

3. The process according to claim 2, wherein the lipid is selected from a vegetable oil, animal fat and fish oil.

4. The process according to claim 1, wherein the coagulating protein is a casein selected from the group consisting of micellar casein, non-micellar casein, sodium caseinate, calcium caseinate, potassium caseinate and magnesium caseinate.

5. The process according to claim 1, wherein the anti-coagulating protein is a non-dairy protein which is an anti-coagulating protein according to the Gastric Digestion Test of Example 1, and/or a combination of such non-dairy protein with whey protein.

6. The process according to claim 1, wherein the mixture has a weight ratio of the coagulating protein to the anti-coagulating protein of between 19:1 and 1:1.

7. The process according to claim 1, further comprising homogenising the first and/or second liquid component.

8. The process according to claim 1, further comprising, before mixing (c), drying the heat-sterilised first liquid component and/or the heat-sterilised second liquid component to obtain a powder.

9. The process according to claim 1, further comprising (d) drying the mixture to obtain a powder.

10. The process according to claim 1, further comprising adding at least 1 wt % of one or more lipids and carbohydrates, relative to the total dry weight of the mixture; and/or at least 0.1 wt % of dietary fibres, relative to the total dry weight of the mixture; or a combination thereof, to the components when heat-sterilizing the first liquid component and/or when heat-sterilising the second liquid component, and/or while mixing the first component with the second component.

11. The process according to claim 10, further comprising adding at least 10 wt % of one or more lipids and carbohydrates, relative to the total dry weight of the mixture; and/or at least 1 wt % of dietary fibres, relative to the total dry weight of the mixture; or a combination thereof, to the components when heat-sterilizing the first liquid component and/or when heat-sterilising the second liquid component, and/or while mixing the first component with the second component.

12. The process according to claim 1, wherein the first liquid component comprises less than 15 wt % anti-coagulating protein.

13. The process according to claim 1, wherein the anti-coagulating protein is selected from Fabaceae proteins.

14. The process according to claim 1, wherein the anti-coagulating protein is a pea protein or a soybean protein.

15. A dry or liquid composition obtained by the process according to claim 1.

16. A method for reducing, preventing or treating gastro-intestinal reflux, intestinal discomfort, reflux, aspiration pneumonia, high gastric residual volume, vomiting, nausea, bloating, digestive discomfort, gastrointestinal cramping, colics, coagulation in the upper gastrointestinal tract and/or delayed gastric emptying, the method comprising administering to a subject in need thereof a composition obtained by the process of claim 1.

17. A method for reducing or preventing coagulation in the upper gastrointestinal tract in a person, the method comprising administering to the person a composition obtained by the process of claim 1.

* * * * *